US007888392B2

(12) United States Patent
Kamiya et al.

(10) Patent No.: US 7,888,392 B2
(45) Date of Patent: Feb. 15, 2011

(54) OINTMENT

(75) Inventors: Akihiko Kamiya, Toshima-ku (JP);
Yoshie Shinohara, Toshima-ku (JP);
Takayuki Sato, Toshima-ku (JP); Kaori Nishizaki, Toshima-ku (JP); Akiko Miwa, Minato-ku (JP); Takatoshi Iida, Yokohama (JP)

(73) Assignee: Taisho Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 11/884,265

(22) PCT Filed: Feb. 14, 2006

(86) PCT No.: PCT/JP2006/302531

§ 371 (c)(1),
(2), (4) Date: Aug. 14, 2007

(87) PCT Pub. No.: WO2006/085655

PCT Pub. Date: Aug. 17, 2006

(65) Prior Publication Data

US 2008/0167379 A1    Jul. 10, 2008

(30) Foreign Application Priority Data

Feb. 14, 2005    (JP) ............. 2005-036095

(51) Int. Cl.
*A61K 31/557*    (2006.01)
(52) U.S. Cl. ................................. 514/573
(58) Field of Classification Search ............ None
See application file for complete search history.

(56) References Cited

U.S. PATENT DOCUMENTS

| | | | | |
|---|---|---|---|---|
| 5,385,907 | A | * | 1/1995 | Asakura et al. ............ 514/291 |
| 6,617,353 | B1 | * | 9/2003 | Ito et al. .................... 514/557 |
| 2005/0009917 | A1 | | 1/2005 | Sato et al. |
| 2005/0192357 | A1 | | 9/2005 | Arai et al. |

FOREIGN PATENT DOCUMENTS

| | | |
|---|---|---|
| EP | 0 737 676 A1 | 10/1996 |
| JP | 59-128327 A | 7/1984 |
| JP | 04-243827 A | 8/1992 |
| JP | 07-233144 A | 9/1995 |
| JP | 2005-247842 A | 9/2005 |
| JP | 2005-247843 A | 9/2005 |
| WO | WO 2004/014394 A1 | 2/2004 |

OTHER PUBLICATIONS

Ansel et al.: Pharmaceutical Dosage Forms and Drug Delivery Systems, 5th Ed., p. 320-322 and p. 324-325, 1990.*
Ikuo Suzuki, et al.: "Dai Juyon Kaisei Nippon Yakkyokukata Kaisetsusho (Hirokawa shoten)" 2001, pp. A44-A47.
Mitsuo Matsumoto, et al.: "Yakuzaigaku Manual (Nanzando)" First Edition, Mar. 20, 1989, pp. 101-102.

* cited by examiner

*Primary Examiner*—Ardin Marschel
*Assistant Examiner*—Bong-Sook Baek
(74) *Attorney, Agent, or Firm*—Sughrue Mion, PLLC

(57)    ABSTRACT

An ointment containing a compound represented by formula (I):

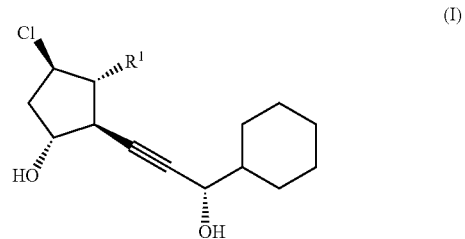

[wherein $R^1$ represents any group of
a group represented by the formula:

—$(CH_2)_4$—S—$CH_2$—$CO_2H$, a group represented by the formula:

—$(CH_2)_4$—S—$CH_2$—$CO_2CH_3$, a group represented by the formula:

—$(CH_2)_4$—C≡C—$CO_2H$, a group represented by the formula:

—$CH_2$—S—$(CH_2)_2$—S—$CH_2$—$CO_2H$, and a group represented by the formula:

—$CH_2$—S—$(CH_2)_4$—$CO_2H$], and an oleaginous base, is an ointment containing a compound which is effective for atopic symptoms, and is an ointment having low skin irritancy and excellent storage stability, thus, can be used as a pharmaceutical product effective for the pruritus caused by atopy or the like.

4 Claims, 3 Drawing Sheets

OINTMENT

TECHNICAL FIELD

The present invention relates to an ointment containing a pharmaceutical agent having an antipruritic effect, which ointment has low skin irritancy and excellent storage stability.

BACKGROUND ART

In recent years, with an increasing number of patients suffering from allergic diseases including atopy, there is a demand on a medicine having excellent effects thereon.

As therapeutic agents for atopy, steroid drugs, immunosuppressants and the like have been conventionally used. However, these medicaments do not have sufficient effect, and are not satisfactory even in terms of side effects or the like.

Among them, a medicament containing a compound represented by formula (I), which has an excellent effect on the pruritus caused by atopy:

[Chem. 1]

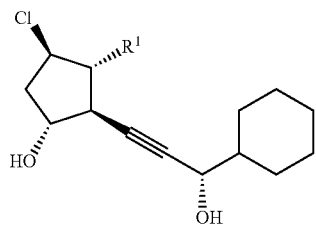

(I)

[wherein $R^1$ represents any group of:

a group represented by the formula:

—$(CH_2)_4$—S—$CH_2$—$CO_2H$, a group represented by the formula:

—$(CH_2)_4$—S—$CH_2$—$CO_2CH_3$, a group represented by the formula:

—$(CH_2)_4$—C≡C—$CO_2H$, a group represented by the formula:

—$CH_2$—S—$(CH_2)_2$—S—$CH_2$—$CO_2H$, and a group represented by the formula:

—$CH_2$—S—$(CH_2)_4$—$CO_2H$], or the like as an active ingredient, has been disclosed (Patent Document 1).

External preparations are available in numerous formulations such as ointment, cream, lotion, tape, and the like, and it is required to select a formulation and a base that are suitable for the use, depending on the skin condition. In the case of an external preparation applicable to atopic dermatitis, ointment is often selected from the fact that the patients originally have dry skin, or that ointment can be safely used even in those sites that have been wetted due to scratching or the like.

[Patent Document 1] International Patent Application Publication No. WO 2004/014394

DISCLOSURE OF THE INVENTION

Problems to be Solved by the Invention

The inventors of the present invention have attempted, in order to provide a medicament having an excellent effect on the pruritus caused by atopy, to prepare an ointment containing the compound represented by formula (I).

In the case of preparing an ointment, use of a hydrophilic base would be contemplated as the prime choice in terms of the feasibility in blending with the main drug, which serves the role of the base, or the problem of percutaneous absorbability, however, as hydrophilic bases often require surfactants or preservatives, when those are causative of skin irritation, it is possible that application thereof to atopic dermatitis would be limited. Furthermore, the active ingredient of the invention could not attain sufficient storage stability in an ointment using a hydrophilic base.

Moreover, with regard to an oleaginous base, since the solubility of the compound represented by formula (I) therein is insufficient, it has been difficult to dissolve the compound represented by formula (I) in the preparation.

An object of the present invention is to provide an ointment in which the compound represented by formula (I) having an excellent effect is stably blended.

Means to Solve the Problems

The inventors of the present invention have repeated investigation in various ways to solve the above problems, and as a result, found that an oleaginous ointment having excellent storage stability for the compound represented by formula (I) and low skin irritancy can be obtained by dispersing the compound represented by formula (I) in an oleaginous base which does not dissolve the compound represented by formula (I), in a solid state or in an oily state. In addition, the inventors also found that the ointment thus obtained was an ointment having excellent releasability of the active ingredient from the base, despite that the active ingredient is dispersed in a solid state or in an oily state, and thus completed the present invention.

Thus, the present invention is an ointment containing a compound represented by formula (I):

[Chem. 2]

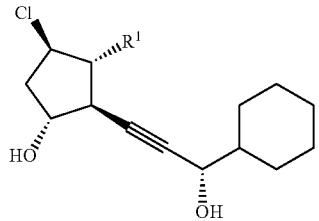

(I)

[wherein $R^1$ represents any group of a group represented by the formula:

—$(CH_2)_4$—S—$CH_2$—$CO_2H$, a group represented by the formula:

—$(CH_2)_4$—S—$CH_2$—$CO_2CH_3$, a group represented by the formula:

—$(CH_2)_4$—C≡C—$CO_2H$, a group represented by the formula:

—$CH_2$—S—$(CH_2)_2$—S—$CH_2$—$CO_2H$, and a group represented by the formula:

—$CH_2$—S—$(CH_2)_4$—$CO_2H$], and an oleaginous base.

ADVANTAGE OF THE INVENTION

The ointment of the present invention was found to have excellent storage stability with respect to the compound represented by formula (I) and low skin irritancy, as well as excellent drug releasability and sense of use.

BEST MODE FOR CARRYING OUT THE INVENTION

Figure 1:
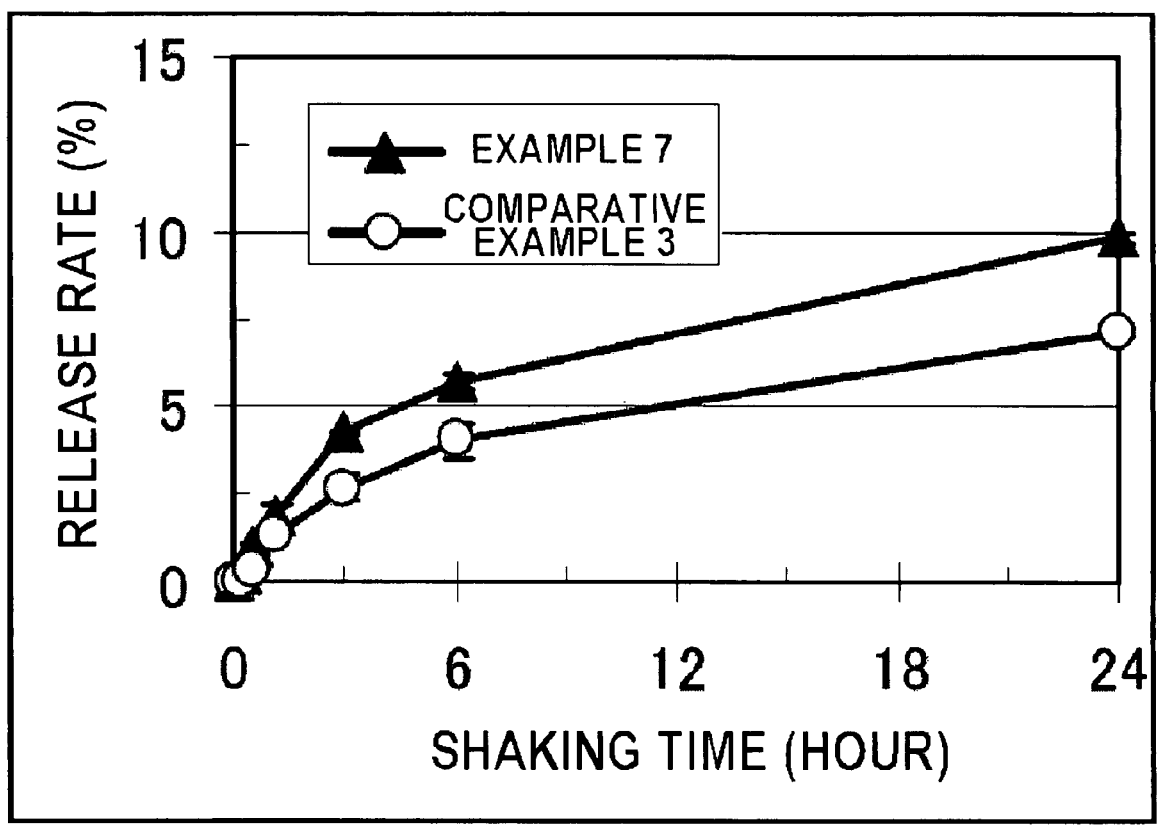
FIG. 1 A graph showing the rates of drug release from ointments at pH 7.4, which ointments were filled in semipermeable membranes and shaken in phosphate buffer solution at 37° C. The vertical axis in the graph represents the drug release rate, while the horizontal axis represents time.

The family of compounds represented by formula (I), which is blended as an active ingredient in the present invention, is such that any member therefrom exhibits excellent effects and can be favorably prepared into the ointment of the present invention, but in particular, a compound represented by formula (II):

[Chem. 3]

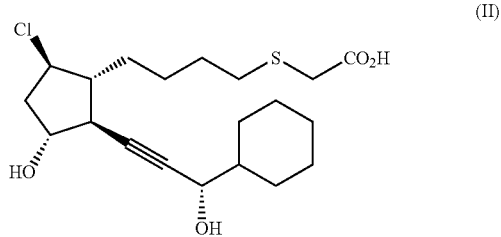

(II)

is excellent in stability, skin irritation, drug releasability and the sense of use, thus it being particularly preferred.

In general, drugs at their low concentrations frequently deteriorate in stability and homogeneity. According to the present invention, however, it is possible to provide preparations having excellent stability, homogeneity and drug releasability even at extremely low concentrations. Since the active ingredient of the present invention exhibits its effect even in low concentration ranges in the ointment, the present invention can be applied as long as the active ingredient is in an amount in the range where the effect is manifested. But, a preferred range is from 0.000001% to 0.1% of the ointment as a whole, while a more preferred range is from 0.00001% to 0.01%, and a particularly preferred range is from 0.0001% to 0.001%.

For the oleaginous base used in the present invention, those commonly used in oily ointments can be used, but the base is preferably selected from hydrocarbons, fatty acid esters, or animal and plant oils, and is more preferably one or two or more selected from the group consisting of white petrolatum, gelated hydrocarbons, light liquid paraffin, liquid paraffin, diisopropyl adipate, isopropyl palmitate, isopropyl myristate, octyl dodecyl myristate and medium-chain fatty acid triglycerides.

Among these oleaginous bases, a composition containing saturated hydrocarbons is preferred, and in particular, white petrolatum, a combination of white petrolatum and light liquid paraffin, a combination of white petrolatum and liquid paraffin, a combination of white petrolatum and paraffin, a combination of white petrolatum and squalane, a combination of white petrolatum and methylpolysiloxane or gelated hydrocarbon is more preferred. In the case of using light liquid paraffin, liquid paraffin, paraffin, squalane or methylpolysiloxane in combination with white petrolatum for the oleaginous base, the blending amount of the light liquid paraffin, liquid paraffin, paraffin, squalane or methylpolysiloxane is preferably 10% or less of the whole ointment.

It is preferable for the oleaginous base of the present invention to use a material which has been purified by removing impurities, in terms of securing the stability of the component. In particular, a white petrolatum which has been purified by removing impurities that are absorbable to silica gel through column chromatography or the like, is preferred.

The ointment of the present invention is characterized in that the compound of formula (I) is dispersed in an oleaginous base in a solid state or in an oily state, and can be prepared as an ointment having excellent storage stability.

Here, the term "disperse in an oily state" means a state in which the compound of formula (I) is dispersed in the oleaginous base not as crystals but in an oily state. This state can be confirmed by observing with a microscope.

The method for preparing an ointment as such is as follows. As a dispersion medium for the compound of formula (I) white petrolatum, light liquid paraffin, liquid paraffin, paraffin, squalane, methylpolysiloxane, medium-chain fatty acid triglyceride, isopropyl myristate, isopropyl palmitate and the like are used, and they are added after heating, if necessary, to obtain a mixed dispersion. The resulting mixed dispersion is added to and mixed with an oleaginous base with stirring, thus to disperse the components homogeneously. At this time, it is preferable to add the mixed dispersion while maintaining the temperature of the oleaginous base in a range which is lower than the melting point of the compound represented by formula (I), and higher than the melting point of the oleaginous base. Particularly, in the case of using the compound represented by formula (II), the temperature is preferably maintained at 45° C. to 55° C. Subsequently, optional components are added according to necessity, and mixed with stirring while cooling to room temperature, thus, an ointment having the components homogeneously dispersed can be obtained. Additionally, it is also possible to prepare the ointment by dispersing the compound represented by formula (I) in an oleaginous base, without providing a separate dispersion medium.

The ointment of the present invention can appropriately contain, in addition to the compound represented by formula (I) and the oleaginous base, an antioxidant such as butylhydroxyanisole or dibutylhydroxytoluene, a stabilizer such as EDTA-2Na, and the like within the scope of not impairing the effect of the present invention.

By using the ointment preparation of the present invention, not only a preparation having low skin irritancy and good storage stability with regard to the compound could be obtained, but onset of the effect was also confirmed, as the ointment showed a drug releasability equivalent to that of a dissolved type preparation, even though the active ingredient was dispersed in the oleaginous base in a solid state or in an oily state.

EXAMPLES

Hereinafter, the present invention will be described in more detail with reference to Examples and Test Examples.

Example 1

90 g of white petrolatum (Perfecta, manufactured by Crompton Corp.) was heated to melt in a water bath, and was maintained at about 50° C. A homogeneous dispersion formed by adding in advance 10 mg of the compound represented by formula (II) to 10 g of medium-chain fatty acid triglyceride, was homogeneously mixed with the molten white petrolatum. The mixture was gradually cooled and thoroughly stirred until hardened, thus to prepare an ointment.

Example 2

An ointment was prepared in the same manner as in Example 1, except that the medium-chain fatty acid triglyceride was replaced by isopropyl myristate.

Example 3

An ointment was prepared in the same manner as in Example 1, except that the medium-chain fatty acid triglyceride was replaced by isopropyl palmitate.

Example 4

90 g of white petrolatum was heated to melt in a water bath, and was maintained at about 50° C. A homogeneous dispersion formed by adding in advance 10 mg of the compound represented by formula (II) to 10 g of white petrolatum, was homogeneously mixed with the molten white petrolatum. The mixture was gradually cooled and thoroughly stirred until hardened, thus to prepare an ointment.

Example 5

200 g of white petrolatum was heated to 80° C., and was purified by means of a column charged with 50 g of silica gel. An ointment was prepared in the same manner as in Example 4, except that the white petrolatum of Example 4 was replaced by this purified white petrolatum.

Example 6

An ointment was prepared in the same manner as in Example 4, except that the white petrolatum of Example 4 was replaced by a commercially available hydrogenated purified white petrolatum (Sunwhite P-150, manufactured by Nikko Rica Corp.).

Example 7

An ointment was prepared in the same manner as in Example 4, except that the white petrolatum of Example 4 was replaced by a commercially available purified white petrolatum (Crolatum V, manufactured by Croda Japan Co., Ltd.).

Example 8

85 g of a commercially available purified white petrolatum (Crolatum V, manufactured by Croda Japan Co., Ltd.) and 5 g of solid paraffin were heated to melt in a water bath, and were maintained at about 50° C. A homogeneous dispersion formed by adding in advance 10 mg of the compound represented by formula (II) to 10 g of purified white petrolatum, was homogeneously mixed with the molten white petrolatum mixture. The mixture was gradually cooled and thoroughly stirred until hardened, thus to prepare an ointment.

Example 9

85 g of a commercially available purified white petrolatum (Crolatum V, manufactured by Croda Japan Co., Ltd.) and 5 g of solid paraffin were heated to melt in a water bath, and were maintained at about 50° C. A homogeneous dispersion formed by adding in advance 10 mg of the compound represented by formula (II) to 10 g of liquid paraffin, was homogeneously mixed with the molten white petrolatum mixture. The mixture was gradually cooled and thoroughly stirred until hardened, thus to prepare an ointment.

Comparative Example 1

25 g of white petrolatum, 20 g of stearyl alcohol, 40 g of polyoxyethylene hydrogenated castor oil 60, and 1 g of glyceryl monostearate were heated to melt in a water bath. The molten mixture was maintained at about 75° C. while stirring, and to this, a liquid formed by dissolving in advance 10 mg of the compound represented by formula (II), 0.01 g of methyl parahydroxybenzoate and 0.01 g of propyl parahydroxybenzoate in 12 g of propylene glycol, adding the resulting solution to 37.8 g of purified water, and heating the mixture to about 75° C., was added. The mixture was stirred to emulsify, subsequently cooled, and thoroughly stirred until hardened, thus to prepare an ointment.

Comparative Example 2

50 g of Macrogol 4000 and 50 g of Macrogol 400 were heated to melt in a water bath at 65° C., and then 10 mg of the compound represented by formula (II) was added and melted therein. The mixture was cooled to room temperature and thoroughly stirred until hardened, thus to prepare an ointment.

Comparative Example 3

90 g of white petrolatum was heated to melt in a water bath, and was maintained at about 50° C. A liquid formed by dissolving in advance 10 mg of the compound represented by formula (II) in 10 g of 1,3-butylene glycol, and heating the solution to about 50° C., was added to the molten white petrolatum. The mixture was homogeneously dispersed using a homomixer, cooled to room temperature, and thoroughly stirred until hardened, thus to prepare an ointment.

Comparative Example 4

An ointment was obtained in the same manner as in Comparative Example 3, except that 1,3-butylene glycol of Comparative Example 3 was replaced by 10 g of propylene glycol.

Comparative Example 5

An ointment was obtained in the same manner as in Comparative Example 3, except that 1,3-butylene glycol of Comparative Example 3 was replaced by 10 g of glycerin.

Test Example 1

To confirm the storage stability of the compound represented by formula (II) in the preparation, the content (%) of the compound after a storage of 2 weeks at 50° C. against the content at the time of initiation was determined. The results are presented in Table 1.

TABLE 1

|  | STORAGE AT 50° C. | |
| --- | --- | --- |
|  | UPON INITIATION | 2 WEEKS |
| EXAMPLE 1 | 100.0 | 92.1 |
| EXAMPLE 4 | 100.0 | 98.1 |
| EXAMPLE 7 | 100.0 | 98.3 |
| COMPARATIVE EXAMPLE 1 | 100.0 | 77.0 |
| COMPARATIVE EXAMPLE 2 | 100.0 | 23.9 |
| COMPARATIVE EXAMPLE 3 | 100.0 | 38.2 |

As is obvious from the table, the ointments of Comparative Example 1 and Comparative Example 2 using hydrophilic bases resulted in low values such as 77.0% and 23.9%, respectively, while the ointment of Comparative Example 3 which used an oleaginous base, but had the compound represented by formula (II) present in the base in a dissolved state, resulted in 38.2%. On the other hand, for the ointments of Example 1, Example 4 and Example 7, the values were as high as 92.1%, 98.1% and 98.3%, respectively. Thus, it was confirmed that storage stability was improved by dispersing the compound represented by formula (II) in an oleaginous base in an oily state or in a solid state.

Test Example 2

To more closely examine the storage stability of the ointments in which the compound represented by formula (II) was dispersed in oleaginous bases in an oily state or in a solid state, the ointments of Example 4, Example 5, Example 6 and Example 7 were prepared, and the content (%) of the compound after a storage of 4 weeks at 50° C. and the content (%) of a degradation product, S-oxide form, were determined. The results are presented in Table 2.

There were no large decreases in the content, and with regard to the S-oxide form, which is a degradation product causing problems in view of storage stability of the present ointment, the amount of increment was smaller in the ointments of Example 5 and Example 7 which used purified white petrolatum. Therefore, it was confirmed that the storage stability of the compound represented by formula (II) was further enhanced by purifying the saturated hydrocarbons.

Test Example 3

To evaluate the drug releasability from the ointments shown in Example 7 and Comparative Example 3, the preparations were filled in semi-permeable membranes, and were shaken in phosphate buffer solution at pH 7.4 at 37° C. The results are presented in FIG. 1. As is obvious from the figure, the compound represented by formula (II) was slowly released into the buffer solution, and the release rate from the ointment of Example 7 was equal to or greater than that of the ointment of Comparative Example 3. From this, it could be seen that although the active ingredient is dispersed in an oleaginous base in a solid state or in an oily state, the drug is released at a rate equal to or greater than that of a dissolved type preparation.

Test Example 4

Figure 2:
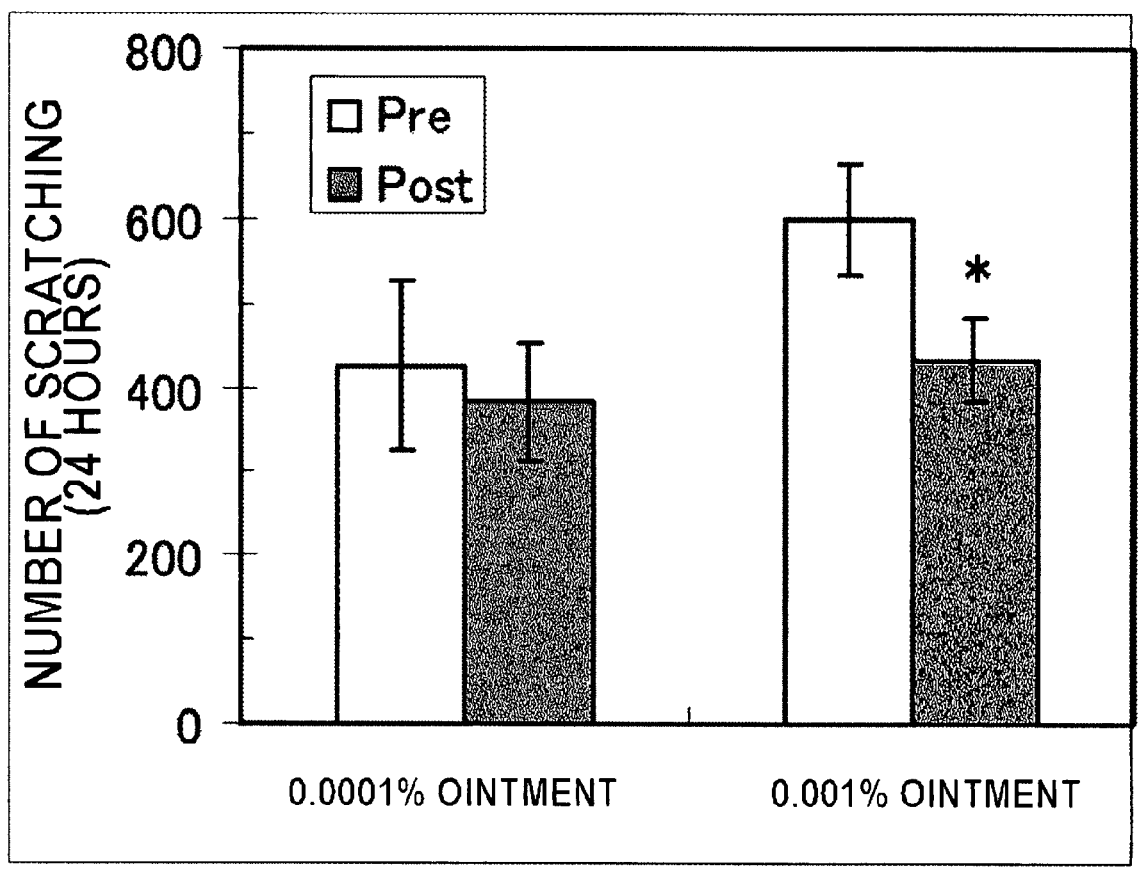
FIG. 2 A graph showing the number of scratching action (average value±SE, n=8) when a present ointment was applied to NC/Nga mice. The graph shows that in the case of the 0.001% ointment, the number of scratching significantly ($P<0.05$) decreased after the application.
Figure 3:
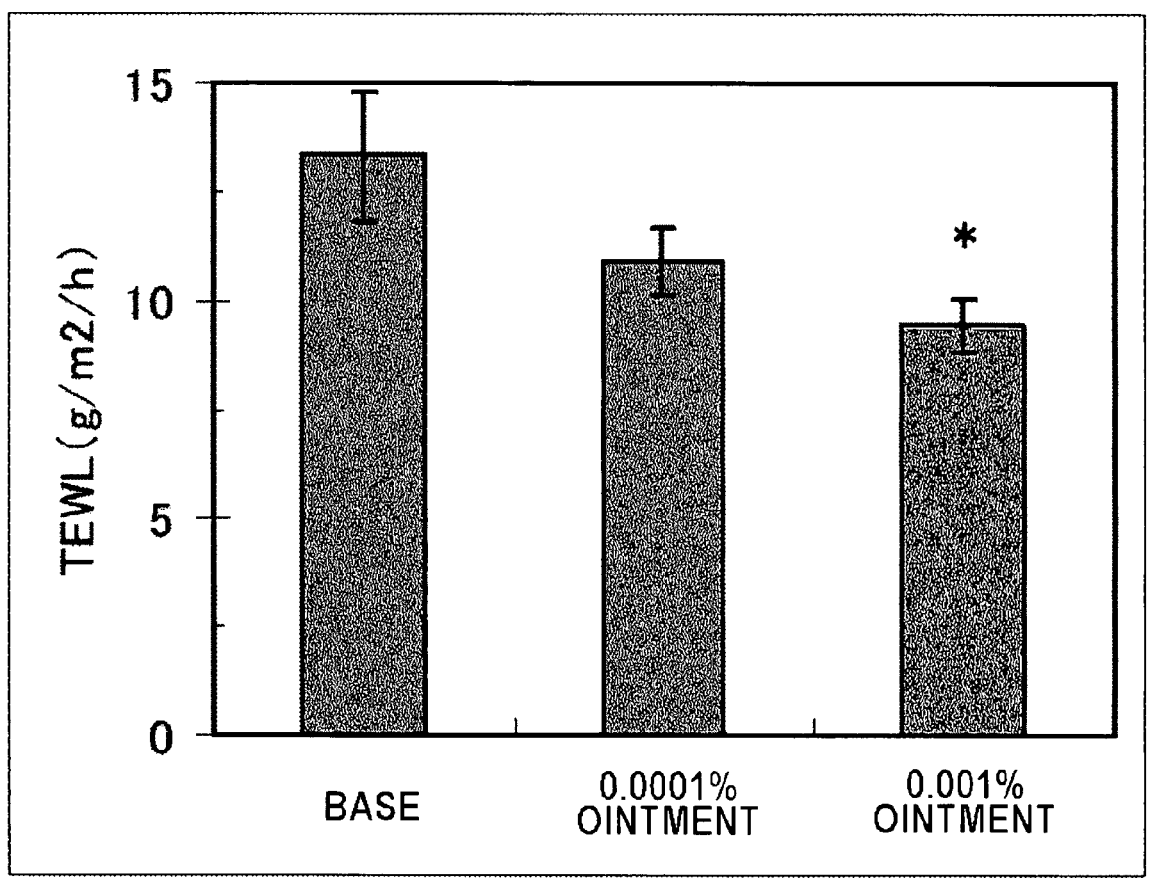
FIG. 3 A graph showing the amount of transdermal evaporation of water (TEWL, average value±SE, n=8) when a present ointment was applied to BALB/c mice having the skin barrier destroyed by chafing. It can be seen that when compared with the case where only the base was applied, applying a 0.001% ointment led to a significant ($P<0.05$) decrease in TEWL.

According to the methods described in the literature (Japanese Laid-open patent publication Nos. 2005-247843 and 2005-247842), measurements of the spontaneous action of scratching and the amount of transdermal water evaporation were performed with regard to the compound represented by formula (II). A test was performed, using ointments prepared in the same manner as in Example 4 to have the compound represented by formula (II) at concentrations of 0.0001% and 0.001%. As a result, a decrease in the scratching action (FIG. 2), which implies an antipruritic effect, and a decrease in the amount of transdermal water evaporation (FIG. 3), which implies a skin barrier restoring effect, were recognized. From this, the preparation of the present invention was shown to manifest sufficient effect.

Example 10

95 g of a commercially available purified white petrolatum (Crolatum V, manufactured by Croda Japan Co., Ltd.) was heated to melt in a water bath, and was maintained at about 50° C. A homogeneous dispersion formed by adding in advance 10 mg of the compound represented by formula (II) to 5 g of light liquid paraffin, was homogeneously mixed with the molten white petrolatum. The mixture was gradually cooled and thoroughly stirred until hardened, thus to prepare an ointment.

TABLE 2

|  | CONTENT AGAINST INITIAL CONTENT (%) | | | CONTENT OF S-OXIDE FORM (%) | | |
| --- | --- | --- | --- | --- | --- | --- |
|  | UPON INITIATION | 2 WEEKS | 4 WEEKS | UPON INITIATION | 2 WEEKS | 4 WEEKS |
| EXAMPLE 4 | 100.0 | 98.1 | 96.1 | 1.03 | 2.81 | 3.41 |
| EXAMPLE 5 | 100.0 | 102.6 | 103.1 | 0.71 | 0.96 | 1.34 |
| EXAMPLE 6 | 100.0 | 95.0 | 94.2 | 1.19 | 4.25 | 4.04 |
| EXAMPLE 7 | 100.0 | 98.3 | 95.7 | 0.68 | 1.22 | 2.24 |

Example 11

92 g of a commercially available purified white petrolatum (Crolatum V, manufactured by Croda Japan Co., Ltd.) and 3 g of solid paraffin were heated to melt in a water bath, and were maintained at about 50° C. A homogeneous dispersion formed by adding in advance 10 mg of the compound represented by formula (II) to 5 g of light liquid paraffin, was homogeneously mixed with the molten white petrolatum mixture. The mixture was gradually cooled and thoroughly stirred until hardened, thus to prepare an ointment.

Example 12

95 g of a commercially available purified white petrolatum (Crolatum V, manufactured by Croda Japan Co., Ltd.) was heated to melt in a water bath, and was maintained at about 50° C. A homogeneous dispersion formed by adding in advance 10 mg of the compound represented by formula (II) to 5 g of liquid paraffin, was homogeneously mixed with the molten white petrolatum. The mixture was gradually cooled and thoroughly stirred until hardened, thus to prepare an ointment.

Example 13

95 g of a commercially available purified white petrolatum (Crolatum V, manufactured by Croda Japan Co., Ltd.) was heated to melt in a water bath, and was maintained at about 50° C. A homogeneous dispersion formed by adding in advance 10 mg of the compound represented by formula (II) to 5 g of squalane was homogeneously mixed with the molten white petrolatum. The mixture was gradually cooled and thoroughly stirred until hardened, thus to prepare an ointment.

Example 14

92 g of a commercially available purified white petrolatum (Crolatum V, manufactured by Croda Japan Co., Ltd.) and 3 g of solid paraffin were heated to melt in a water bath, and were maintained at about 50° C. A homogeneous dispersion formed by adding in advance 10 mg of the compound represented by formula (II) to 5 g of methylpolysiloxane, was homogeneously mixed with the molten white petrolatum mixture. The mixture was gradually cooled and thoroughly stirred until hardened, thus to prepare an ointment.

Example 15

95 g of a commercially available purified white petrolatum (Crolatum V, manufactured by Croda Japan Co., Ltd.) was heated to melt in a water bath, and was maintained at about 50° C. A homogeneous dispersion formed by adding in advance 10 mg of the compound represented by formula (II) to 5 g of purified olive squalane, was homogeneously mixed with the molten white petrolatum. The mixture was gradually cooled and thoroughly stirred until hardened, thus to prepare an ointment.

Example 16

95 g of a commercially available purified white petrolatum (Crolatum V, manufactured by Croda Japan Co., Ltd.) and 3 g of solid paraffin were heated to melt in a water bath, and were maintained at about 50° C. A homogeneous dispersion formed by adding in advance 10 mg of the compound represented by formula (II) to 5 g of squalane, was homogeneously mixed with the molten white petrolatum. The mixture was gradually cooled and thoroughly stirred until hardened, thus to prepare an ointment.

Example 17

92 g of a commercially available purified white petrolatum (Crolatum V, manufactured by Croda Japan Co., Ltd.) was heated to melt in a water bath, and was maintained at about 50° C. A homogeneous dispersion formed by adding in advance 10 mg of the compound represented by formula (II) to 5 g of methylpolysiloxane, was homogeneously mixed with the molten white petrolatum. The mixture was gradually cooled and thoroughly stirred until hardened, thus to prepare an ointment.

Example 18

92 g of a commercially available purified white petrolatum (Crolatum V, manufactured by Croda Japan Co., Ltd.) and 3 g of solid paraffin were heated to melt in a water bath, and were maintained at about 50° C. A homogeneous dispersion formed by adding in advance 10 mg of the compound represented by formula (II) to 5 g of methylpolysiloxane, was homogeneously mixed with the molten white petrolatum. The mixture was gradually cooled and thoroughly stirred until hardened, thus to prepare an ointment.

Test Example 5

To confirm the storage stability of the compound represented by formula (II) in the preparation, the content (%) of the compound after a storage at 40° C. and 75% RH against the content at the time of initiation, was determined. The results are presented in Table 3.

TABLE 3

| | STORAGE AT 40° C. AND 75% RH | | | | |
|---|---|---|---|---|---|
| | UPON INITIATION | 1 MONTH | 2 MONTHS | 3 MONTHS | 6 MONTHS |
| EXAMPLE 10 | 100.0 | 100.4 | 100.7 | 104.8 | 98.2 |
| EXAMPLE 11 | 100.0 | 97.7 | 100.1 | 102.3 | 97.4 |
| EXAMPLE 12 | 100.0 | 96.4 | 98.7 | 97.7 | — |
| EXAMPLE 13 | 100.0 | 99.6 | 99.0 | 98.4 | — |
| EXAMPLE 14 | 100.0 | 100.6 | 98.6 | 99.1 | — |
| EXAMPLE 15 | 100.0 | 99.6 | 99.0 | 98.4 | — |
| EXAMPLE 16 | 100.0 | 99.6 | 99.0 | 98.4 | — |
| EXAMPLE 17 | 100.0 | 100.7 | 100.7 | 98.0 | — |
| EXAMPLE 18 | 100.0 | 100.6 | 98.6 | 99.1 | — |

As is obvious from the table, the respective samples of the Examples exhibited high stability. From this, it was confirmed that the storage stability of the compound represented by formula (II) was improved by dispersing the compound in oleaginous bases in a solid state.

Examples 19 to 22

92 g of a commercially available purified white petrolatum (Crolatum V, manufactured by Croda Japan Co., Ltd.) and 3 g of solid paraffin were heated to melt in a water bath, and were maintained at about 50° C. A homogeneous dispersion formed by adding in advance 10 mg of the compound represented by formula (II) to the respective additives in their respective amounts of addition indicated in Table 4, was homogeneously mixed with the molten white petrolatum. The mixture was gradually cooled and thoroughly stirred until hardened, thus to prepare an ointment.

Test Example 6

To confirm the storage stability of the compound represented by formula (II) in the preparation, the contents (%) of the compound after storages at 40° C. and 75% RH, and at 50° C. against the content at the time of initiation, was determined. The results are presented in Table 4.

TABLE 4

|  | TYPE OF ADDITIVE | AMOUNT OF ADDITION | UPON INITIATION | STORAGE AT 40° C. AND 75% RH 1 MONTH | STORAGE AT 50° C. 1 MONTH |
| --- | --- | --- | --- | --- | --- |
| EXAMPLE 19 | DIISOPROPYL ADIPATE | 5 g | 100.0 | 97.9 | 97.9 |
| EXAMPLE 20 | DIISOPROPYL MYRISTATE | 10 g | 100.0 | 99.1 | 97.3 |
| EXAMPLE 21 | DIISOPROPYL PALMITATE | 5 g | 100.0 | 93.3 | 98.9 |
| EXAMPLE 22 | DIETHYL SEBACATE | 5 g | 100.0 | 98.9 | 93.9 |

As is obvious from the table, it was confirmed that when the compound represented by formula (II) was dissolved in the oleaginous base, the respective additives resulted in high storage stability.

Example 23

475 g of a commercially available purified white petrolatum (Crolatum V, manufactured by Croda Japan Co., Ltd.) was heated to melt in a water bath, and was maintained at about 50° C. A homogeneous dispersion formed by adding in advance 5 mg of the compound represented by formula (II) to 25 g of light liquid paraffin, was homogeneously mixed with the molten white petrolatum. The mixture was gradually cooled and thoroughly stirred until hardened, thus to prepare an ointment.

Example 24

1620 g of a commercially available purified white petrolatum (Crolatum V, manufactured by Croda Japan Co., Ltd.) was heated to melt in a water bath, and was maintained at about 50° C. A homogeneous dispersion formed by adding in advance 18 mg of the compound represented by formula (II) to 180 g of the same white petrolatum, was homogeneously mixed with the molten white petrolatum. The mixture was gradually cooled and thoroughly stirred until hardened, thus to prepare an ointment.

Test Example 7

To confirm the storage stability of the compound represented by formula (II) in the preparation, the contents (%) of the compound after a storage at 40° C. and 75% RH, or at 25° C. against the content at the time of initiation, was determined. The results are presented in Table 5.

TABLE 5

|  | UPON INITIATION | STORAGE AT 40° C. AND 75% RH 1 MONTH | STORAGE AT 25° C. 3 MONTHS |
| --- | --- | --- | --- |
| EXAMPLE 23 | 100.0 | 92.2 |  |
| EXAMPLE 24 | 100.0 |  | 100.7 |

As is obvious form the table, it was confirmed that the compound represented by formula (II) was stable in the drugs.

Example 25

475 g of a commercially available purified white petrolatum (Crolatum V, manufactured by Croda Japan Co., Ltd.) was heated to melt in a water bath, and was maintained at about 50° C. A homogeneous dispersion formed by adding in advance 0.5 mg of the compound represented by formula (II) to 25 g of light liquid paraffin, was homogeneously mixed with the molten white petrolatum. The mixture was gradually cooled and thoroughly stirred until hardened, thus to prepare an ointment.

Example 26

450 g of a commercially available purified white petrolatum (Crolatum V, manufactured by Croda Japan Co., Ltd.) was heated to melt in a water bath, and was maintained at about 50° C. A homogeneous dispersion formed by adding in advance 0.5 mg of the compound represented by formula (II) to 50 g of the same white petrolatum, was homogeneously mixed with the molten white petrolatum. The mixture was gradually cooled and thoroughly stirred until hardened, thus to prepare an ointment.

INDUSTRIAL APPLICABILITY

According to the present invention, it is now possible to provide an ointment having an excellent effect on the pruritus caused by atopy, and thus the ointment can be used as a pharmaceutical product effective for the pruritus caused by atopy or the like.

The invention claimed is:

1. An oleaginous ointment consisting essentially of a compound represented by formula (II):

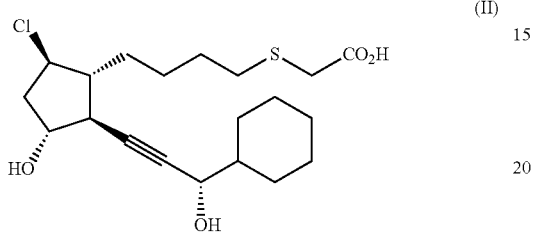

and an oleaginous base,
wherein the compound represented by formula (II) is dispersed in the oleaginous base in a solid state or in an oily state, such that the compound is not dissolved in the oleaginous base; and
wherein the compound represented by formula (II) is present in the ointment in the range of about 0.000001% to 0.1% by weight;
wherein the oleaginous base comprises a white petrolatum purified by removing impurities; and,
wherein the ointment is produced by adding a dispersion obtained by dispersing the compound represented by formula (II) in the oleaginous base, to the oleaginous base maintained at a temperature of 45° C. or higher and 55° C. or lower, and mixing the dispersion and the oleaginous base with stirring.

2. A method for producing an oleaginous ointment consisting essentially of a compound represented by formula (II):

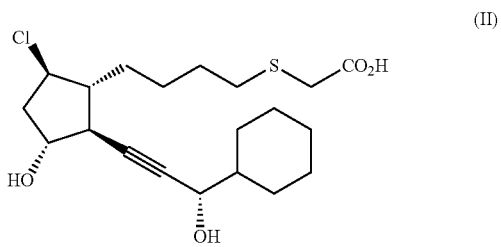

and an oleaginous base,
wherein the compound represented by formula (II) is dispersed in the oleaginous base in a solid state or in an oily state, such that the compound is not dissolved in the oleaginous base;
wherein the compound represented by formula (II) is present in the ointment in the range of about 0.000001% to 0.1% by weight; and
wherein the oleaginous base comprises a white petrolatum purified by removing impurities,
the method comprising:
(i) dispersing the compound represented by formula (II) in the oleaginous base in a solid or oily state to obtain a dispersion;
(ii) adding the dispersion to the oleaginous base maintained at a temperature of 45° C. or higher and 55° C. or lower; and
(iii) mixing the dispersion and the oleaginous base with stirring.

3. The ointment according to claim 1,
wherein the oleaginous base is a white petrolatum which has been purified by removing impurities that are absorbable to silica gel.

4. The ointment according to claim 1,
wherein the oleaginous base further comprises one or more selected from the group consisting of light liquid paraffin, liquid paraffin, paraffin, squalane, methylpolysiloxane, and gelated hydrocarbons.

* * * * *